US00PP11764P2

(12) United States Plant Patent
Trees

(10) Patent No.: US PP11,764 P2
(45) Date of Patent: Feb. 6, 2001

(54) GERANIUM PLANT NAMED 'BALFANSAMI'

(75) Inventor: Scott C. Trees, Nipomo, CA (US)

(73) Assignee: Ball FloraPlant, a division of Ball Horticultural Co., West Chicago, IL (US)

( * ) Notice: Under 35 U.S.C. 154(b), the term of this patent shall be extended for 0 days.

(21) Appl. No.: 09/255,634

(22) Filed: Feb. 20, 1999

(51) Int. Cl.[7] ..... A01H 5/00

(52) U.S. Cl. ..... Plt./327

(58) Field of Search ..... Plt./327, 325, 328

*Primary Examiner*—Bruce R. Campell
*Assistant Examiner*—Wendy A Baker
(74) *Attorney, Agent, or Firm*—C. A. Whealy

(57) ABSTRACT

A new and distinct cultivar of Geranium plant named 'Balfansami', characterized by its numerous semi-double light salmon pink-colored flowers; upright growth habit; basal branching and vigorous; and medium green leaves with a distinct zonation pattern.

1 Drawing Sheet

BACKGROUND OF THE INVENTION

The present invention relates to a new and distinct cultivar of Geranium plant, botanically known as *Pelargonium*× *hortorum*, and hereinafter referred to by the cultivar name Balfansami.

The new Geranium is a product of a planned breeding program conducted by the Inventor in Arroyo Grande, Calif. The objective of the breeding program was to develop new cultivars with freely-branching growth habit, dark green-colored foliage, uniform flowering, rounded umbels, and interesting flower and foliage colors.

The new Geranium originated from a cross made by the Inventor of the *Pelargonium*×*hortorum* cultivar Isabell, disclosed in U.S. Plant Pat. No. 7,080, as the male, or pollen parent, with the proprietary *Pelargonium*×*hortorum* selection BFP-1215 as the female, or seed parent. The cultivar Balfansami was discovered and selected by the Inventor as a flowering plant within the progeny of the stated cross in a controlled environment in Arroyo Grande, Calif., in December, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balfansami'. These characteristics in combination distinguish 'Balfansami' as a new and distinct cultivar:

1. Numerous semi-double light salmon-colored flowers.
2. Upright growth habit.
3. Basal branching and vigorous.
4. Medium green leaves with a distinct zonation pattern.

Compared to plants of the new Geranium's sibling Balfanflam (U.S. Plant Patent application submitted concurrently with this application), plants of the new Geranium are more compact, have more flowers per umbel, have shorter peduncles, and differ in flower color.

The new Geranium can be compared to the cultivar, Eclipse Light Salmon, disclosed in U.S. Plant Pat. No. 7,926. However, in side-by-side comparisons conducted in Arroyo Grande, Calif., plants of the new Geranium differ from plants of the cultivar Eclipse Light Salmon in the following characteristics:

1. Plants of the new Geranium are less compact than plants of the cultivar Eclipse Light Salmon.
2. Plants of the new Geranium are more vigorous than plants of the cultivar Eclipse Light Salmon.
3. Plants of the new Geranium have smaller leaves and shorter leaf petioles than plants of the cultivar Eclipse Light Salmon.
4. Leaf zonation pattern of plants of the new Geranium are maroon in color whereas leaf zonation pattern of plants of the cultivar Eclipse Light Salmon is dark green. Additionally the zonation pattern is narrower on plants of the new Geranium compared to plants of the cultivar Eclipse Light Salmon.
5. Plants of the new Geranium have more flowers per umbel than plants of the cultivar Eclipse Light Salmon.
6. Flower color of plants of the new Geranium is darker than flower color of plants of the cultivar Eclipse Light Salmon.
7. Sepal color of plants of the new Geranium is maroon whereas sepal color of plants of the cultivar Eclipse Light Salmon is green.

A detailed comparison of plants of the cultivar Balfansami and the cultivar Eclipse Light Salmon, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'Balfansami'. Flower and foliage colors in the photograph may appear different from the actual colors due to light reflectance.

DETAILED BOTANICAL DESCRIPTION

The cultivar Balfansami has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20 to 22° C., night temperatures about 18 to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium×hortorum* cultivar Balfansami.

Parentage:

*Male parent.*—*Pelargonium×hortorum* cultivar Isabell, disclosed in U.S. Plant Pat. No. 8,070.

*Female parent.*—Proprietary *Pelargonium×hortorum* selection BFP-1215.

Propagation:

*Type cutting.*—Terminal cuttings.

*Time to initiate roots.*—About 7 days at 18° C.

*Time to develop roots.*—About 21 days at 18° C.

*Rooting habit.*—Fibrous and freely branching.

Plant description:

*General appearance.*—Upright growth habit. Appropriate for 10 and 12.5-cm containers.

*Crop time.*—Starting with a rooted cutting, about eight weeks are required to produced a finished flowering plant in 10-cm container.

*Growth and branching habit.*—Vigorous and basal branching with about three or four lateral branches at the base. Pinching, that is, removal of the terminal apex, is usually not required.

*Plant height (to top of foliage).*—About 13 to 14 cm.

*Plant width.*—About 19 to 24 cm.

*Lateral branches.*—Length: About 7 to 10 cm. Internode length: About 1.5 to 2 cm. Color: 146B; streaks, 187A.

*Foliage description.*—Leaves simple, generally symmetrical, abundant, opposite. Quantity of leaves per lateral branch: About 12 to 13. Length: About 4.5 to 5 cm. Width: About 8 to 8.5 cm. Shape: Reniform. Apex: Rounded. Base: Cordate. Margin: Crenate. Venation: Palmate. Texture: Both surfaces pubescent; leathery. Color: Young foliage, upper surface: 137C. Young foliage, lower surface: 137D. Fully expanded foliage, upper surface: 137B with distinct zonation pattern, close to 187A, about 1.5 to 2 cm in width. Fully expanded foliage, lower surface: 137C. Venation, upper surface: 137C. Venation, lower surface: 137D. Petiole: Length: About 4 to 5 cm. Diameter: About 2.5 to 3 mm. Color: 137B.

Flower description:

*Flower type and habit.*—Light salmon-colored flowers. Freely and continuously flowering. Flowers arranged in substantially hemispherical umbels arising from apical leaf axils. Umbels displayed above or beyond the foliage. At full flowering, usually about three or four open umbels and about one to three developing umbels per plant. Flowers semi-double and round. Umbels persistent. Not fragrant.

*Flowering season.*—Year-round under greenhouse conditions. In the garden, flowering is continuous from spring until fall.

*Umbels.*—Number of flowers per umbel: About 50 to 60. Diameter: About 11 to 12 cm. Height: About 6.5 to 9 cm.

*Flowers.*—Diameter: About 4.5 to 5.5 cm. Depth (height): About 2 to 2.5 cm.

*Flower buds.*—Length: About 1.4 to 1.6 cm. Diameter: About 8 to 11 mm. Shape: Oval, pointed.

*Petals.*—Quantity: About 5 to 7 petals and about 3 or 5 elongated petaloids per flower. Arrangement: Imbricate. Length: About 2.5 to 2.6 cm. Width: About 2 to 2.5 cm. Shape: Obovate. Apex: Rounded. Base: Attenuate. Margin: Entire. Aspect: Upright, flowers cup-shaped. Texture: Satiny. Color: When opening and fully opened, upper surface: Base, 43C, fading to 43D towards margin; venation, 41C; with subsequent development, 50B. When opening and fully opened, lower surface: 43D.

*Sepals.*—Quantity: About 5, not imbricate. Length: About 7 to 8 mm. Width: About 3 to 4 mm. Shape: Lanceolate. Apex: Pointed. Margin: Entire. Texture: Pilose. Color: Upper surface: Between 183A and 184A with faint undertones of 143A. Lower surface: 183C with faint undertones of 143C.

*Peduncle (umbel stem).*—Length: About 13.5 to 15 cm. Angle: Erect. Strength: Moderately strong. Texture: Pubescent. Color: 137B; streaks, 187A.

*Pedicel (individual flower stem).*—Length: About 3 to 4 cm. Angle: Upright to outward. Strength: Moderately strong. Texture: Pubescent. Color, mature: 183A.

*Reproductive organs.*—Androecium: Anther size: About 2 mm. Anther color: 64A. Pollen color: 169 C. Gynoecium: Ovary color: Green.

Disease resistance: Resistance to pathogens common to Pelargonium has not been observed.

Seed development: Seed production has not been observed.

CHART A

| CHARACTERISTIC | 'BALFANSAMI' | 'ECLIPSE LIGHT SALMON' |
|---|---|---|
| PLANT HEIGHT (to top of foliage) | About 13 to 14 cm | About 10 to 11 cm |
| PLANT WIDTH | About 19 to 24 cm | About 19 to 21 cm |
| VIGOR | Vigorous | Moderately vigorous |
| LEAF LENGTH | About 4.5 to 5 cm | About 5 to 6 cm |
| LEAF WIDTH | About 8 to 8.5 cm | About 8 to 10 cm |
| LEAF COLOR, FULLY EXPANDED, UPPER SURFACE | 137B | 136A |
| LEAF COLOR, FULLY EXPANDED, LOWER SURFACE | 137C | 137B |
| LEAF ZONATION PATTERN/COLOR | Distinct zonation pattern; Close to 187A | Distinct zonation pattern; 139A |
| WIDTH OF ZONATION PATTERN | About 1.5 to 2 cm | About 2 to 3 cm |
| PETIOLE LENGTH | About 4 to 5 cm | About 6 to 7 cm |
| NUMBER OF FLOWERS PER UMBEL | About 50 to 60 | About 40 to 50 |
| PETAL COLOR, FULLY OPENED, UPPER SURFACE | Base, 43C, fading to 43D towards margin; venation, 41C | Base, 43D, fading to 38B towards margin; venation, 47D |
| PETAL COLOR, FULLY OPENED, LOWER SURFACE | 43D | 41D |
| SEPAL COLOR, UPPER SURFACE | Between 183A and 184A, with faint undertones of 143A | 143A |
| SEPAL COLOR, LOWER SURFACE | 183C, with faint undertones of 143C | 143C |
| POLLEN COLOR | 169C | 169A |

It is claimed:

1. A new and distinct cultivar of Geranium plant named 'Balfansami', as illustrated and described.

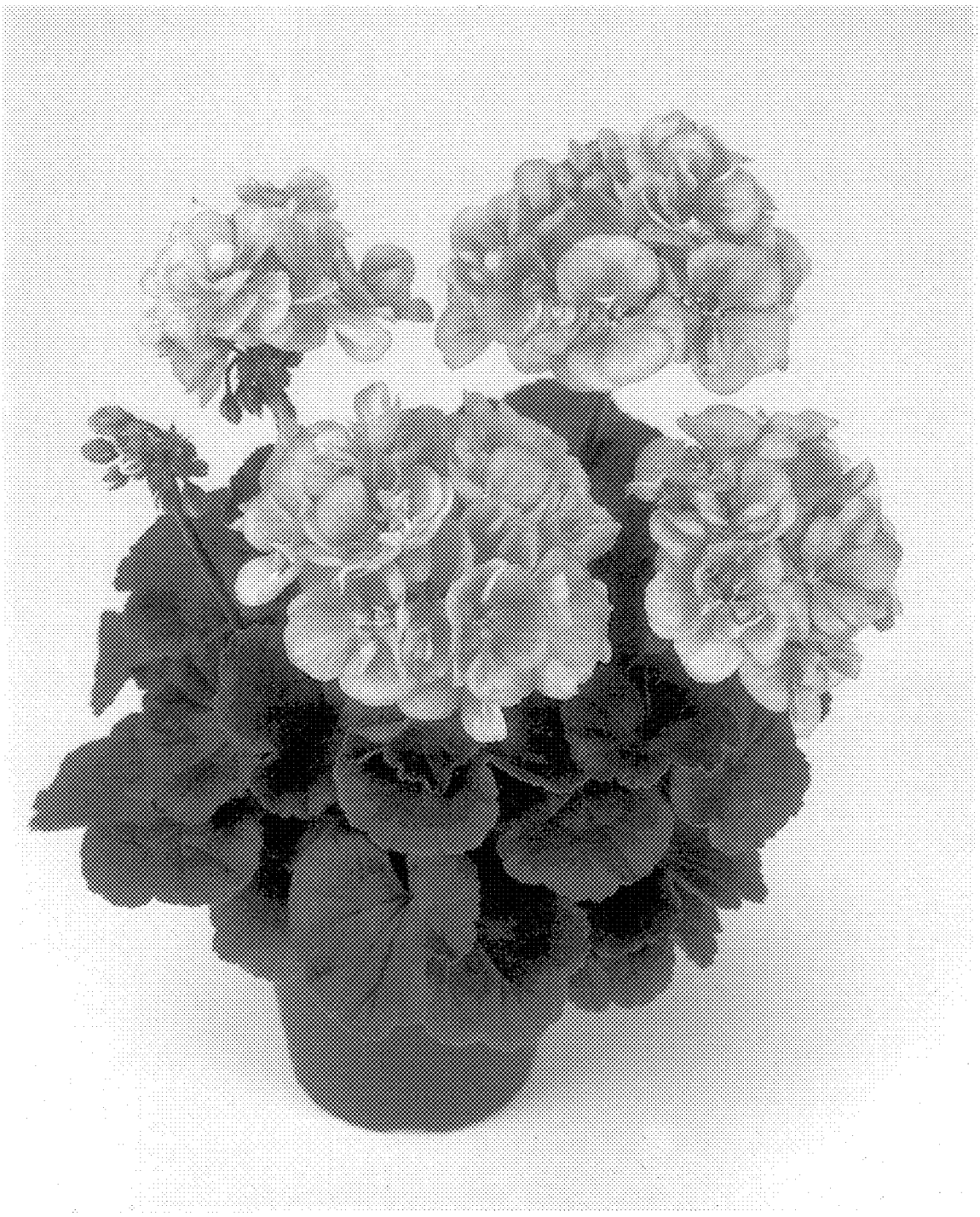

* * * * *